United States Patent [19]
Guala

[11] Patent Number: 4,929,427
[45] Date of Patent: May 29, 1990

[54] EQUIPMENT FOR MEASURING THE ERYTHROSETTLING RATE OF BLOOD USING PIPETTES

[76] Inventor: Piergiacomo Guala, Via Trotti, 20, 15100 Alessandria, Italy

[21] Appl. No.: 188,973

[22] Filed: May 2, 1988

[51] Int. Cl.⁵ .............................................. B01L 9/06
[52] U.S. Cl. .................................. 422/100; 422/104; 422/300; 422/310; 211/74; 211/79; 211/80; 206/366; 206/443; 206/565
[58] Field of Search .............. 422/100, 104, 297, 310, 422/300; 206/366, 443, 565

[56] References Cited
U.S. PATENT DOCUMENTS

| | | | |
|---|---|---|---|
| 3,302,452 | 2/1967 | Leslie | 422/100 X |
| 3,802,844 | 4/1974 | Sendra et al. | 422/104 |
| 4,142,633 | 3/1979 | Raghavachari et al. | 422/100 X |
| 4,453,639 | 6/1984 | Sharma | 422/104 X |

Primary Examiner—Robert J. Warden
Assistant Examiner—Lynn M. Kummert
Attorney, Agent, or Firm—Notaro & Michalos

[57] ABSTRACT

Equipment for measuring the rate of erythrosettling of blood comprises a plurality of pipettes, a rack for holding the pipettes upright, and a closure element for the bottom end of each pipette. The rack includes an elongated pedestal, a portal attached to the pedestal, a plurality of seats adapted to receive the pipettes by snap action and formed in the portal, and a bridge element associated with the portal and straddling it. The bridge element is displaceable elastically from a home position to a working position interfering with the pipettes, for simultaneously removing the pipettes from their snap-action holding seats. The invention affords the advantage that the operator is not required to come in contact with the blood being analyzed.

5 Claims, 5 Drawing Sheets

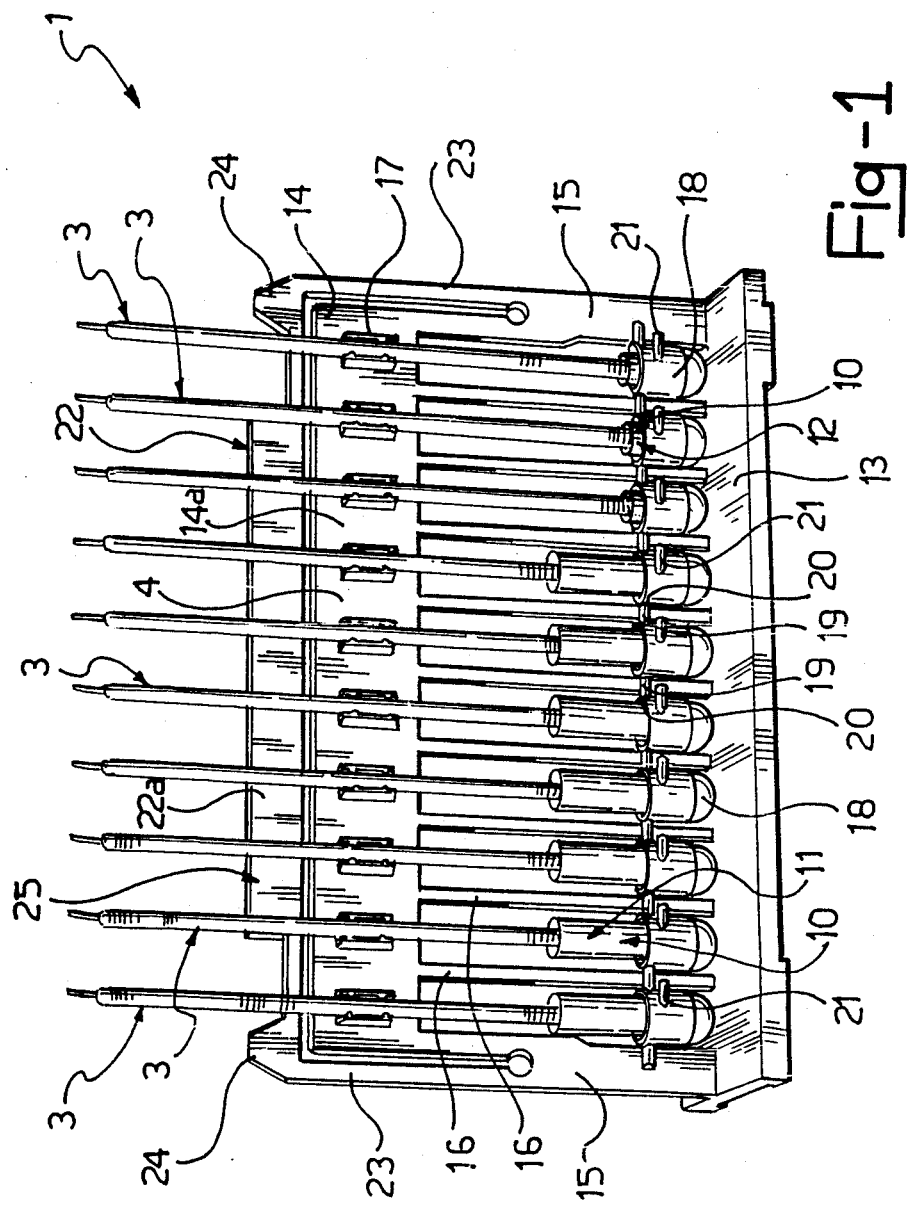

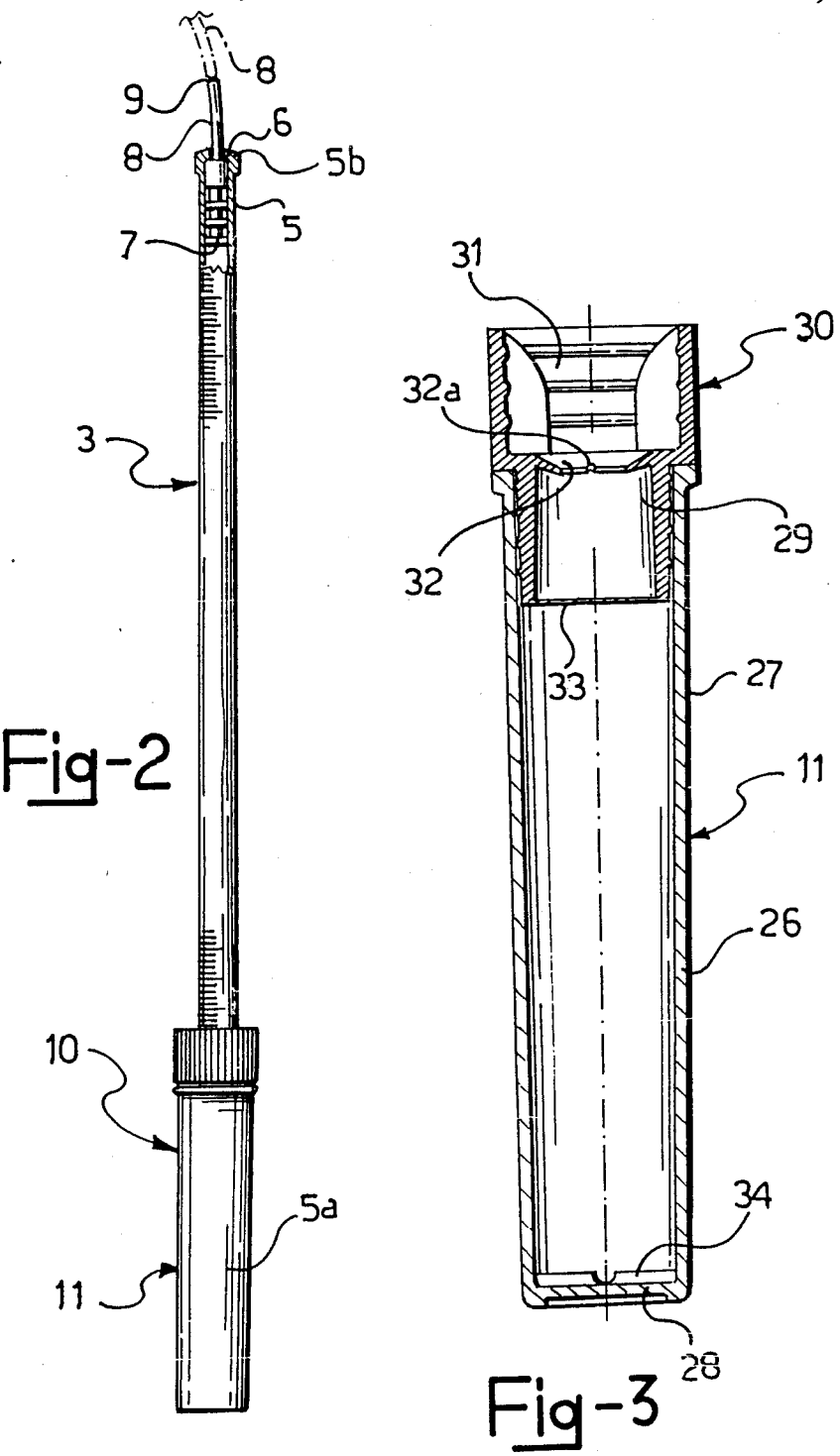

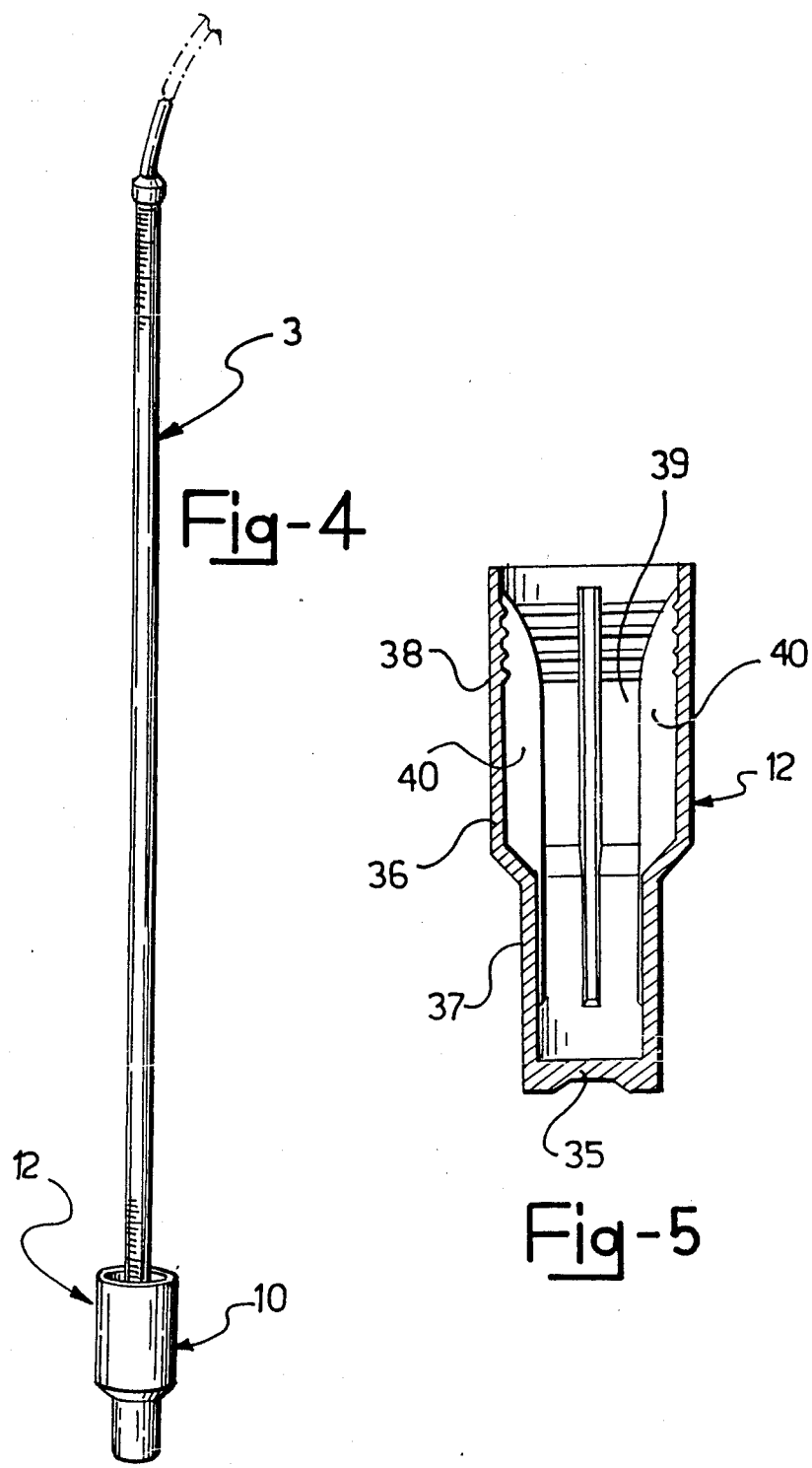

EQUIPMENT FOR MEASURING THE ERYTHROSETTLING RATE OF BLOOD USING PIPETTES

FIELD AND BACKGROUND OF THE INVENTION

This invention relates to equipment for measuring the rate of erythrosettling, of a type which comprises a plurality of pipettes, a rack for holding said pipettes upright, and an element for closing the bottom end of each pipette.

The measurement of erythrosettling rate is known to involve a series of operations ranging from procurement of a blood sample using a syringe to disposal of the pipette after the relevant graduation scale formed on it is read.

In the course of the various operations that the operator is to perform, he/she is exposed to the risk of coming in direct contact with the blood sample to be measured. A number of different expedients have been proposed to restrict the likelihood of direct contact with the blood.

As an example, Italian Patent Application No. 22085-B/83 by this same Applicant discloses a pipette which is filled with a predetermined amount of the blood to be analyzed without requiring, at least during this step, the operator to contact the blood.

However, in performing the other operations, this danger still exists, along with the consequences it entails.

SUMMARY OF THE INVENTION

It is an object of this invention to provide equipment of the type specified above which can reduce the opportunities for the operator to contact the blood.

This object is achieved by equipment as indicated being characterized in that said rack comprises an elongate pedestal, a portal attached to the pedestal, a plurality of seats adapted to receive and hold by snap action pipettes provided in the portal, a bridge element associated with the portal to straddle it, being movable elastically from a home position to a working position where it interferes with said pipettes, for simultaneously removing the pipettes from their snap-action holding seats.

Further features and the advantages of the equipment according to this invention will be apparent from the following detailed description of a preferred embodiment thereof, to be taken by way of example and not of limitation in conjunction with the accompanying drawings, where:

BRIEF DESCRIPTION OF THE DRAWINGS

FIG. 1 is a perspective view of an apparatus according to the invention;

FIG. 2 is an enlarged scale, partly cutaway perspective view of a detail of the equipment shown in FIG. 1;

FIG. 3 is a sectional view, drawn to a much enlarged scale, of a detail of the equipment shown in FIG. 1;

FIG. 4 is an enlarged scale perspective view of a detail of the apparatus of FIG. 1;

FIG. 5 is a perspective view, drawn to a much enlarged scale, of a detail of the apparatus of FIG. 1;

DESCRIPTION OF THE PREFERRED EMBODIMENT

Figure 6:
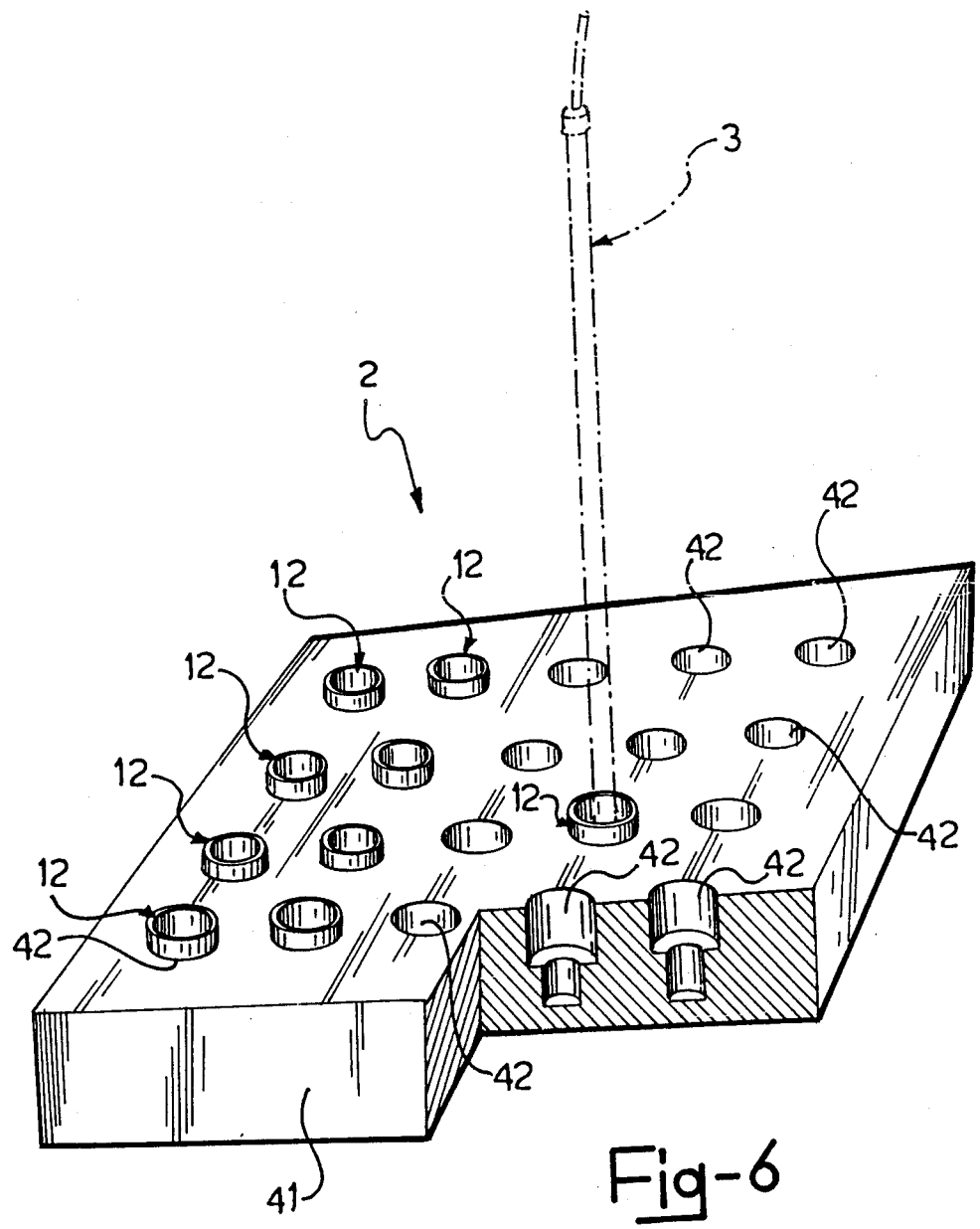
FIG. 6 is a perspective view showing an accessory device to the apparatus of FIG. 1.

With reference to the drawing views, the numeral 1 generally designates an item of equipment for measuring the rate of erythrosettling, and 2 an accessory device thereto.

The equipment 1 comprises a plurality of pipettes, ten in the example shown, which are designated collectively 3, and a rack 4 for holding said pipettes upright at regular pitch distances.

Each pipette 3 comprises a graduated tube 5 having a bottom end 5a and a top end 5b which is formed with a rim 6.

Accommodated slidingly within the tube 4 is a piston 7 having a flexible stem 8 associated therewith, by means of which stem the piston 7 can be driven from the bottom end 5a of the tube 5 to the top end 5b so as to abut the rim 6, for drawing blood to be measured.

A rupture invitation, that is a narrowing section 9, is formed in the stem 8 a short distance away from the piston 7. On the piston 6 stopping against the rim, the stem 8 will break at said narrowing section 9, and the major portion of the stem separates and can be disposed of.

Each pipette 3 is provided with a closure element 10 at its bottom end 5a.

In the example shown, for seven pipettes, the closure element is a test tube 11, whereas for the other "t", it is a cap-type stopper 12.

The rack 4 comprises a pedestal 13 with an elongate shape, and a portal 14 attached to the pedestal 13. The portal 14 has a horizontal section 14a and two vertical posts 15 affixed to the pedestal 13. A plurality of tiny vertical pillars, interleaved with the pipettes and collectively indicated at 16, extend between the pedestal 13 and the horizontal section 14a of the portal 14.

Formed in the front region of the portal 14 are ten holding seats 17 each adapted to receive by snap action and detachably a respective one of the pipettes 3, substantially in a press-button type of interfit.

The rack 4 further comprises ten cradles 18 arranged across the pedestal 13.

Each of these receives the bottom end 5a of a respective pipette 3 complete with its respective closure element 10.

The cradles 18 are provided with trunnions 19, all aligned along a common pivot axis, which are accommodated in bearing seats 20 formed in the pillars 16 and the posts 15 at a short distance from the pedestal. Each cradle 18 also has a lug 21 adapted to engage a pillar 16 or a post 15 in abutting relationship therewith to limit the amplitude of the forward oscillation of the cradle.

The lugs 21 are arranged such that the forward oscillations are all limited to the same amplitude.

The rack 4 also comprises a bridge element 22 associated with and straddling the portal 14.

In particular, the bridge element 22 comprises a horizontal section 22a and two vertical posts 23. The section 22a extends above the section 14a of the portal 14.

The posts 23 have reduced cross-sections, thereby they can be deformed elastically, and juts out of the posts 15 of the portal 14, substantially from a point halfway up.

Figure 7:
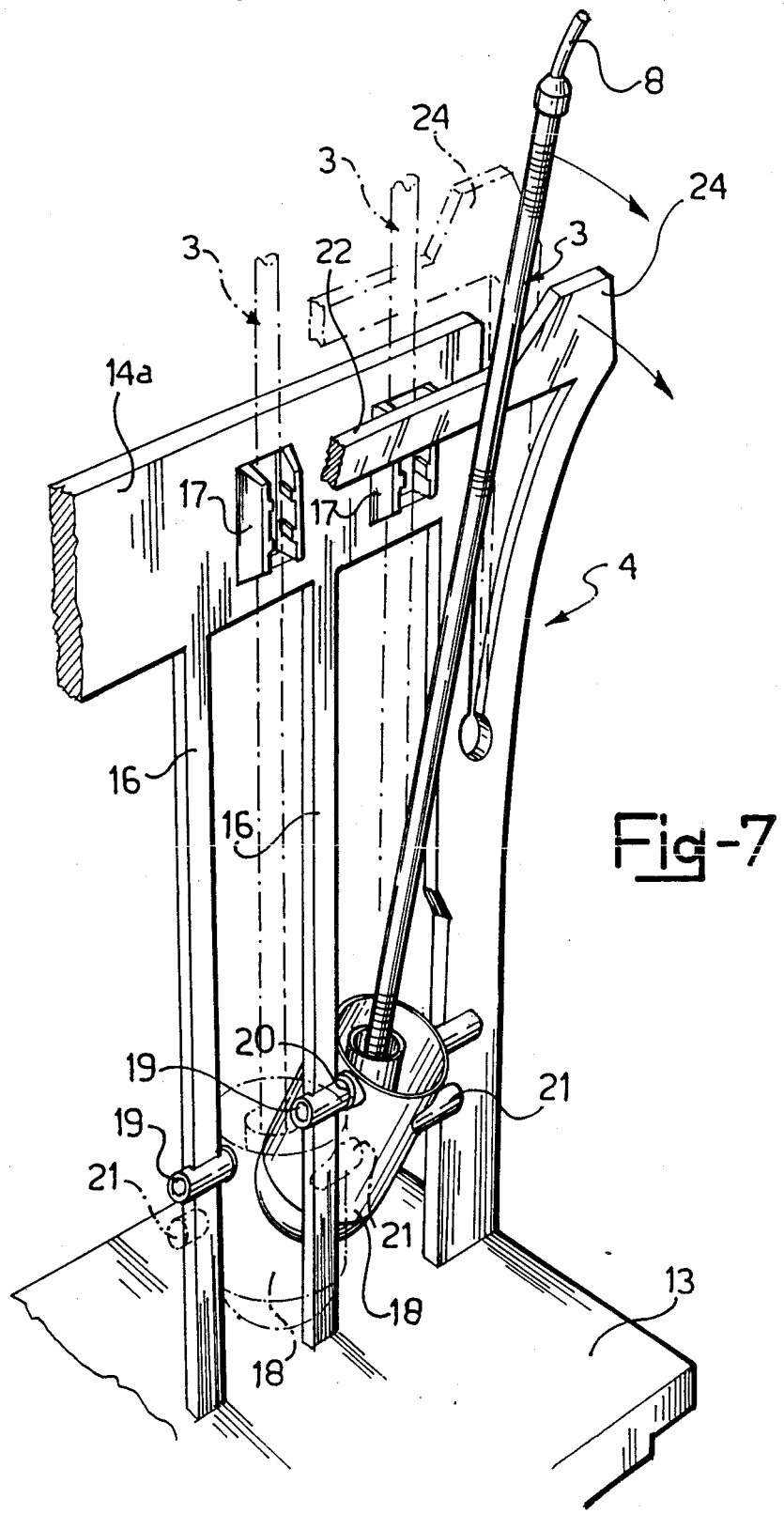
FIG. 7 is a perspective detail view of the apparatus of FIG. 1, shown at a different stage of its operation.

The section 22a is displaceable forward from a home position wherein it lies above the section 14a, to a working position wherein it locates at a predetermined distance therefrom. In that working position, it will interfere with the pipettes 3. The home position is shown in full lines of FIG. 1, and in ghost lines in FIG. 7. The working position is shown in full lines in FIG. 7.

In travelling the path between the home position and the working position, the section 22a will meet with the pipettes 3 and cause them to become detached from their respective seats 17.

The section 22a is provided at both ends with small ears 24 constituting respective handgrips, and along a middle portion, with a strip 25 with stiffening and label-receiving functions.

The test tube 11 comprises a cylindrical container body 26 having a skirt 27 adapted to receive a label, a bottom 28, and a mouth 29. The test tube 11, which contains at first a predetermined amount of a suitable anticoagulant, also comprises a stopper 30 associated with the mouth 29. The stopper 30 is through-penetrated axially by a passage 31 for accommodating a pipette 3 in guided relationship therein.

A circumferential lip 32 is formed internally on said stopper for holding the pipette 3 when the latter is fitted in said passage 31. The lip 32 is formed with a cutout 32a with capillary cross-section to allow air past it but practically inhibit the passage of blood.

A membrane 33 extends to close the passage 31. More specifically, the membrane 33 is a small disk of a laminate plastics/aluminum sheet applied by thermowelding. That membrane can be ruptured by the pipette 3 upon insertion of the latter through the passage 31.

At the bottom 28 there are formed elevations 34 effective to keep the end 5a of the pipette 3 off the bottom.

The cap-type stopper 12 comprises a bottom 35 and a substantially flared out cylindrical skirt 36 having a first section 37 placed on the bottom 35 side and having a small diameter dimension, and a second section 38 having a large diameter.

In the stopper 12, there is formed a seat 39 for receiving the bottom end of the pipette 3. That seat is formed with ribs 40 to make the pipette and cap-type stopper stably unitary.

The apparatus 1 is completed, as an accessory item thereto, by a package 2 for a plurality of cap-type stoppers 12.

The package 2 comprises a supporting plate 41, wherein plural holes 42 are formed which are sized to receive in slight push fit relationship the first section 37 of each stopper 12 arranged with the seat 38 opening upwards.

The operation of the apparatus 1 will be described hereinbelow in conjunction with the operations performed to measure the erythrosettling rate of blood samples.

After drawing a blood sample from a patient by means of a syringe, the blood is injected into a test tube 11 with the stopper 30 removed. The anticoagulant contained in the test tube ensures preservation of the blood sample for sending to a testing laboratory. The pipette 3 is here inserted into the test tube 11 rupturing the membrane 33. By operating the piston 7 through the stem 8, a predetermined amount of the blood is drawn out into the pipette until the piston 7 reaches the rim 6, and the stem 8 is broken.

At this time, the pipette 3, complete with its test tube 4, is placed on the rack 4 by inserting the bottom end thereof carrying the test tube into a respective cradle 18 and pushing the pipette into a respective snap-action holding seat 17.

The operation is repeated until the rack full capacity.

It should be noted that, for tests to be carried out directly at the test laboratory, and lacking test tubes of the type of the test tube 11, the operator may use any available test tube. In that case, once a predetermined amount of the blood has been drawn into the pipette from the test tube, and the test tube has been discarded, the pipette will be fitted with a cap-type stopper 12. To accomplish this, it will be sufficient to insert the bottom end 5a of the pipette 3 into the seat 39 of a cap-type stopper 12 selected from the cap-type stopper plurality made available by the package 2. On withdrawing the pipette, the stopper is picked up from the package.

The pipette 3, now complete with the cap-type stopper 1, is also stored in the rack 4 similarly as above.

On expiration of the time period required for settling, and after the graduated scale on the pipettes has been read for the desired measurement of the erythrosettling rate, the pipettes are disposed of by just taking the rack 4 vertically above a conventional trash bin and dropping them thereinto as a unit.

The pipettes are dropped by acting on the ears 24 so as to move the section 22a forward from the home position into the working position. As a result, the pipettes will come off their holding seats as a unit, tilt jointly forward about the cradle pivot axis which provide, accordingly, a pivot point for the pipettes. The cradles will tilt forward until each of the lugs 21 abuts against a respective one of the pillars 16 or posts 15. At this point, the pipettes will jointly leave the cradles and fall into the trash bin in an orderly fashion.

The main advantage of the equipment according to the invention is that the measurement of the erythrosettling rate of blood samples can be taken without the operator ever coming in contact with the blood being analyzed throughout the operations.

It should be also noted that the equipment according to the invention shows to be constructionally simple; a not negligible advantage for an article which is intended to be mass-produced and mostly to be disposed of after use.

Understandably, to the equipment disclosed in the foregoing, a skilled person in the art may apply numerous modifications and variations without departing from the true scope of the invention as set forth in the appended claims.

I claim:

1. Equipment for measuring the rate of erythrosettling, of a type which comprises in combination a plurality of pipettes, a rack for holding said pipettes upright, and a plurality of elements, each for closing the bottom end of a respective pipette, wherein said rack comprises an elongate pedestal, a portal attached to the pedestal, a plurality of seats constructed to receive and hold by snap action pipettes provided in the portal, a bridge element positioned and arranged to straddle the portal, wherein the bridge element is elastically movable from a home position to a working position to simultaneously remove each of the pipettes from the snap-action holding seats of the rack.

2. Equipment according to claim 1, wherein said rack comprises a plurality of cradles, one for each pipette, carried across the pedestal wherein the bottom end of each pipette is inserted with a respective closure element, each cradle providing a pivot point for the pipette during removal therefrom.

3. Equipment according to claim 2, wherein said closure element for each pipette is a test tube having a bottom and a mouth, and a stopper attached to the mouth and having means defining a passage axially therethrough for guidingly receiving a respective one of the pipettes, and a membrane extending across said passage and constructed and arranged to be ruptured by the pipette.

4. Equipment according to claim 2, wherein said closure element is a cap-type stopper, said cap-type stopper defining a seat for receiving the bottom end of the pipette in a push fit relationship.

5. Equipment according to claim 4, further comprising a support plate for a plurality of cap-type stoppers, said plate having means defining a plurality of holes for receiving said cap-type stoppers in slight push fit relationship with the seat of the stopper opening upwardly.

* * * * *